(12) United States Patent
Igawa et al.

(10) Patent No.: US 12,037,546 B2
(45) Date of Patent: Jul. 16, 2024

(54) METHOD OF ESTIMATING SURFACE TENSION OF COAL AND METHOD OF PRODUCING COKE

(71) Applicant: JFE Steel Corporation, Tokyo (JP)

(72) Inventors: Daisuke Igawa, Tokyo (JP); Yusuke Dohi, Tokyo (JP); Takashi Matsui, Tokyo (JP)

(73) Assignee: JFE Steel Corporation, Tokyo (JP)

(*) Notice: Subject to any disclaimer, the term of this patent is extended or adjusted under 35 U.S.C. 154(b) by 178 days.

(21) Appl. No.: 17/770,354

(22) PCT Filed: Oct. 14, 2020

(86) PCT No.: PCT/JP2020/038828
§ 371 (c)(1),
(2) Date: Apr. 20, 2022

(87) PCT Pub. No.: WO2021/085145
PCT Pub. Date: May 6, 2021

(65) Prior Publication Data
US 2022/0389326 A1  Dec. 8, 2022

(30) Foreign Application Priority Data
Oct. 28, 2019 (JP) .................. 2019-194864

(51) Int. Cl.
*C10B 45/00* (2006.01)
*C10B 57/04* (2006.01)
*G01N 13/00* (2006.01)

(52) U.S. Cl.
CPC .............. *C10B 45/00* (2013.01); *C10B 57/04* (2013.01); *G01N 13/00* (2013.01)

(58) Field of Classification Search
CPC .......... C10B 45/00; C10B 57/04; G01N 13/00
See application file for complete search history.

(56) References Cited

U.S. PATENT DOCUMENTS

| | | | | |
|---|---|---|---|---|
| 4,135,983 A | * | 1/1979 | Kiritani | .................. C10B 55/02 208/22 |
| 9,463,980 B2 | * | 10/2016 | Fukada | ................ G01N 33/222 |

(Continued)

FOREIGN PATENT DOCUMENTS

| | | |
|---|---|---|
| CA | 3 131 778 A1 | 9/2020 |
| CN | 1392222 A | 1/2003 |

(Continued)

OTHER PUBLICATIONS

Examination Report No. 1 for Standard Patent Application dated Mar. 27, 2023, of counterpart Australian Patent Application No. 2020376541.
Decision to Grant Patent dated Sep. 3, 2021, of counterpart Taiwanese Patent Application No. 109136837, along with a Concise Explanation of Relevance to Office Action in English.
Office Action dated Oct. 28, 2023, of counterpart Chinese Patent Application No. 202080072430.8, along with a Concise Explanation of Relevance of the Office Action in English.

(Continued)

*Primary Examiner* — Jonathan Miller
(74) *Attorney, Agent, or Firm* — DLA Piper LLP (US)

(57) ABSTRACT

A method of estimating a surface tension of coal includes subjecting a surface tension, a physical property value representing a coal rank, and a total inert content of each of different brands of coal to multiple regression analysis to determine in advance a regression equation including the surface tension of coal as an objective variable and the physical property value and the total inert content as explanatory variables; and measuring the physical property value and the total inert content of a coal of which the surface tension is to be estimated, and calculating the surface tension of the coal with the measured physical property value and the measured total inert content, and the regression equation.

4 Claims, 2 Drawing Sheets

(56) References Cited

U.S. PATENT DOCUMENTS

| | | | |
|---|---|---|---|
| 9,850,441 B2* | 12/2017 | Fukada | G01N 33/222 |
| 10,144,891 B2* | 12/2018 | Shimoyama | C10B 57/04 |
| 2013/0255142 A1* | 10/2013 | Dohi | C10B 57/06 |
| | | | 44/550 |
| 2015/0039242 A1 | 2/2015 | Fukada et al. | |
| 2015/0040468 A1* | 2/2015 | Shimoyama | C10L 5/04 |
| | | | 44/620 |
| 2015/0047961 A1* | 2/2015 | Fukada | C10B 57/04 |
| | | | 201/1 |
| 2015/0075961 A1* | 3/2015 | Fukada | G01N 13/00 |
| | | | 44/620 |

FOREIGN PATENT DOCUMENTS

| | | |
|---|---|---|
| CN | 102890144 A | 1/2013 |
| CN | 109374479 A | 2/2019 |
| EP | 2 832 822 A1 | 2/2015 |
| EP | 2 985 602 A1 | 2/2016 |
| EP | 3 211 104 A1 | 8/2017 |
| FR | 552049 A | 4/1923 |
| JP | 2014-202711 A | 10/2014 |
| JP | 2014-218648 A | 11/2014 |
| JP | 5737473 B2 | 6/2015 |
| RU | 2640183 C2 | 12/2017 |
| TW | 201319239 A | 5/2013 |
| WO | 2013/145677 A1 | 10/2013 |
| WO | 2013/145678 A1 | 10/2013 |
| WO | 2013/145679 A1 | 10/2013 |
| WO | 2016/063317 A | 4/2016 |
| WO | 2020/179576 A1 | 9/2020 |

OTHER PUBLICATIONS

D. Li, "The Application of Fuzzy Set Methods for Coking Coal Blending on Data Processing and Coal Storage Field Management in Kunming Steel," Coal Quality Technology, No. 2, Mar. 31, 2015, along with an English translation.

Office Action dated Oct. 27, 2022, of counterpart Russian Patent Application No. 2022110688, along with an English translation.

M.A. Duchesne et al., "Slag density and surface tension measurements by the constrained sessile drop method," Article in "Fuel," V. 188, pp. 173-181, Jan. 2017.

M.C. Williams et al., "A simple flotation method for rapidly assessing the hydrophobicity of coal particles," International Journal of Mineral Processing, vol. 20, Issues 1-2, Jun. 1987, pp. 153-157 (First Page Preview).

International Search Report dated Jan. 12, 2021 in counterpart International Application No. PCT/JP2020/038828.

Written Opinion dated Jan. 12, 2021 in counterpart International Application No. PCT/JP2020/038828.

Extended European Search Report dated Oct. 27, 2022, of counterpart European Patent Application No. 20882942.4.

M. Nagayama et al., "Evaluation of Coal Compatibility Effect in Coke Strength by Surface Tension of Semi-coke," ISIJ International, vol. 57, No. 6, pp. 989-995, Retrieved online on Feb. 25, 2022, Japan, in English.

Official Action dated Dec. 15, 2023, of related U.S. Appl. No. 17/770,573.

Official Action dated Mar. 5, 2024, of related U.S. Appl. No. 17/770,573.

Official Action dated Feb. 14, 2024, of related U.S. Appl. No. 17/789,705.

* cited by examiner

METHOD OF ESTIMATING SURFACE TENSION OF COAL AND METHOD OF PRODUCING COKE

TECHNICAL FIELD

This disclosure relates to a method of estimating the surface tension of coal and a method of producing coke.

BACKGROUND

Coke used as a blast furnace raw material for pig-iron production in blast furnaces preferably has high strength. This is because coke having low strength degrades in blast furnaces to inhibit gas permeability in blast furnaces, which hinders stable production of pig iron.

Coke is produced by carbonizing coal. Carbonization is a process of heating coal at a pyrolysis temperature or higher (about 300° C. or higher) in a non-oxidizing atmosphere. Coal that softens and melts at 350° C. to 600° C. in a carbonization process is preferably used as a raw material of coke. When softening and melting, coal powder or particles adhere to and fuse with each other to form lump coke.

To produce coke having high strength, coal particles preferably adhere well to each other. The surface tension of heat-treated coal (semicoke) is used as a physical property value to evaluate the adhesiveness of the coal.

Examples of the method of measuring the surface tension of coal include a capillary-rise method, a maximum bubble pressure method, a drop weight method, a pendant drop method, a ring method, a Wilhelmy method, an advancing/receding contact angle method, a tilting plate method, and a film flotation method. Since coal is composed of various molecular structures and thus expected to have uneven surface tension, the film flotation method in D. W. Fuerstenau: International Journal of Mineral Processing, 20 (1987), 153 or Japanese Patent No. 5737473 expected to evaluate the surface tension distribution is said to be the most reasonable measurement method.

The film flotation method is a technique based on the idea that pulverized sample particles placed in liquid and starting to sink from floating state have the same surface tension as the liquid have. Sample particles are dropped into liquids having various surface tensions, and the mass ratio of sample particles that float in each liquid is determined. The surface tension distribution is obtained from the result. The film flotation method can measure the surface tension of any coal, regardless of the type of coal such as hard coking coal, non- or slightly caking coal, anthracite, and heat-treated coal (semicoke) made by treating such coal with heat.

The film flotation method has a problem of taking a long time (about one day) to measure the surface tension of coal and is not effective in terms of time. The film flotation method also has a problem of a complicated process of measuring the surface tension, and only skilled measurers can stably measure the surface tension.

It could therefore be helpful to provide a method of easily estimating the surface tension of coal.

SUMMARY

We thus provide:

(1) A method of estimating a surface tension of coal includes: subjecting a surface tension, a physical property value representing a coal rank, and a total inert content of each of different brands of coal to multiple regression analysis to determine in advance a regression equation including the surface tension of coal as an objective variable and the physical property value and the total inert content as explanatory variables; and measuring the physical property value and the total inert content of a coal of which the surface tension is to be estimated, and calculating the surface tension of the coal by using the measured physical property value and the measured total inert content, and the regression equation.

(2) In the method of estimating a surface tension of coal according to (1), the physical property value is a mean maximum vitrinite reflectance of the coal.

(3) In the method of estimating a surface tension of coal according to (1) or (2), wherein the surface tension is a surface tension of a semicoke made by heating coal to a temperature of 350° C. or higher and 800° C. or lower.

(4) A method of producing coke includes: blending coals having surface tensions estimated by the method of estimating a surface tension of coal according to any one of (1) to (3) to form a coal blend; and carbonizing the coal blend to produce coke.

The surface tension of coal can easily be estimated by carrying out the method of estimating a surface tension of coal. When the surface tension of coal can easily be estimated in this way, the estimated value of the surface tension can be used to investigate blending of coals, which enables production of coke with high quality.

DETAILED DESCRIPTION

Figure 1:
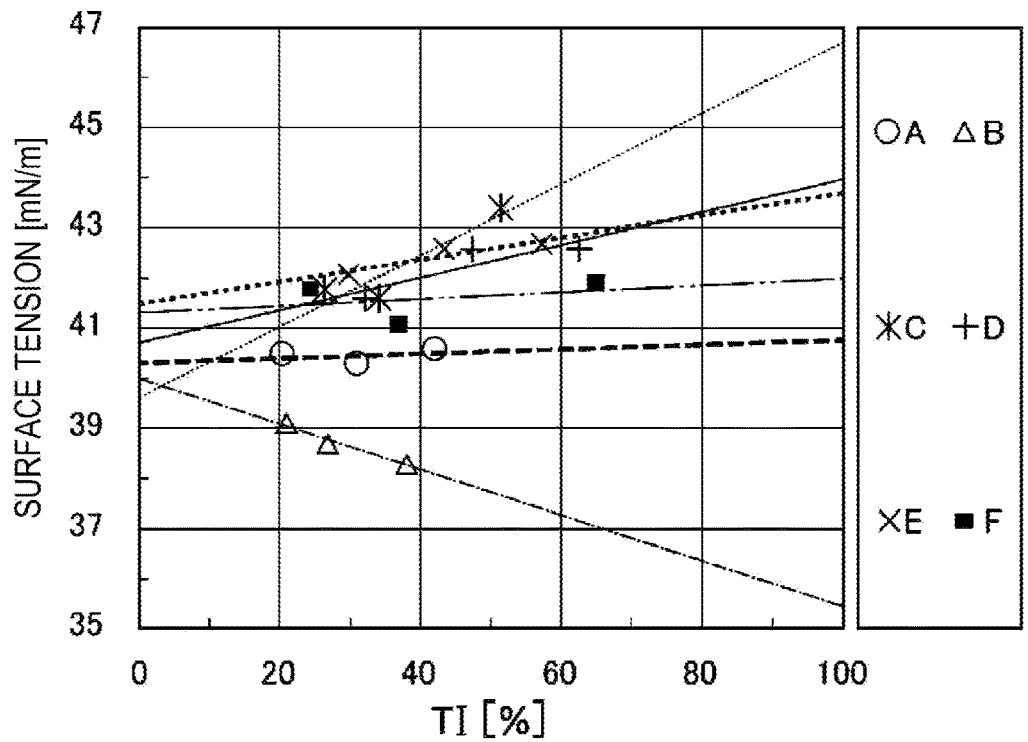
FIG. 1 is a graph showing plots (3 points) of the surface tension of samples having different inert contents and the regression line of the plots for each of samples having different inert contents in 6 brands (A to F) of coal.

Our methods will be described below through examples. We focused on coal components that soften and melt with heat (hereinafter reactives) and coal components that neither soften nor melt with heat (hereinafter inerts). First, the relationship between the surface tensions of the reactives and the inerts and the surface tension of coal will be described.

Since coal inerts are harder than reactives, the inerts tend to concentrate in coarse particles of coal after pulverizing. This tendency is used to prepare samples having different inert contents from the same brand of coal by pulverizing and sifting. The total inert content (hereinafter TI) of each of the samples having different inert contents prepared in this way is measured, and the samples are each treated with heat at a predetermined temperature to form semicokes. The TI is the total inert content defined in JIS M 8816 and indicates the proportion (vol %) of inerts contained in coal.

In this example, the coal of which the surface tension is to be estimated includes heat-treated coal, that is, semicoke. The method of estimating the surface tension of coal according to this example can be applied to coal without a heat treatment as well as semicoke. Since the surface tension of semicoke is particularly useful for predicting coke strength and producing coke with high strength, the method of measuring the surface tension of semicoke, which is heat-treated coal, will be described in this example. In this example, the semicoke is produced in the following (a) to (c):

(a) Pulverizing coal. With regard to the size of particles of pulverized coal, the coal is preferably pulverized to a particle size of 250 µm or less, more preferably pulverized to 200 µm or less, which is the size of particles in proximate analysis of coal described in JIS M8812, to prepare uniform samples from coal which is not uniform in macerals and properties.

(b) Heating the pulverized coal to a temperature of 350° C. or higher and 800° C. or lower at an appropriate heating rate with no air or in an inert gas. The heating rate is preferably set according to the heating rate during production of coke in a coke oven.

(c) Cooling the heated coal in an inert gas to produce semicoke.

With regard to the heating temperature for heating the coal, the coal is preferably heated to a temperature between 350° C. at which the coal starts to soften and melt and 800° C. at which coking is complete, based on the idea that the surface tension has an effect on adhesion between coal particles. However, in a range of heating temperatures of 350° C. to 800° C., the temperature that particularly contributes to adhesion is 350° C. to 550° C. which is a temperature of softening and melting, and the adhesion structure may be set around 500° C. For this, the heating temperature is particularly preferably 480° C. to 520° C., which is around 500° C., and the heating temperature is set to 500° C. in this example. Heating is preferably performed in an inert gas (e.g., nitrogen, argon, helium) atmosphere, which is unreactive with coal.

Cooling is preferably performed in an inert gas atmosphere, which is unreactive with coal. The heat-treated coal is preferably quenched at a cooling rate of 10° C./sec or more. The reason for quenching is to maintain a molecular structure in the reactive state, and the cooling rate is preferably 10° C./sec or higher at which the molecular structure may not change. Quenching may be performed by using liquid nitrogen, iced water, water, or an inert gas such as a nitrogen gas. Quenching is preferably performed by using liquid nitrogen.

The surface tension of the coal can be measured by using the film flotation method described in D. W. Fuerstenau: International Journal of Mineral Processing, 20 (1987), 153. That method can be used for both coal and semicoke made from the coal, and the surface tension distribution can be obtained by using a finely pulverized sample. The mean of the obtained surface tension distribution is defined as a representative value of the surface tension of the sample. The measurement of the surface tension of semicoke using the film flotation method is specifically described in JP '473.

FIG. 1 is a graph showing plots (3 points) of the surface tension (mean of surface tension distribution) of samples having different inert contents and the regression line of the plots for each of 6 brands (A to F) of coal treated with heat at 500° C. (semicokes). In FIG. 1, the horizontal axis represents TI (%), and the vertical axis represents the surface tension (mN/m). Each regression line is a simple regression equation of the surface tension against TI and calculated by using the least squares method to minimize the error between the simple regression equation and each plot. As shown in FIG. 1, an approximately linear relationship is observed between TI and surface tension for each brand of coal. A value corresponding to TI=100 on the regression line is an estimated value of the surface tension at 100% inerts (hereinafter may be referred to as $\gamma_{100}$), and a value corresponding to TI=0 is an estimated value of the surface tension at 100% reactives (hereinafter $\gamma_0$).

FIG. 1 shows that $\gamma_0$ has a tendency of convergence to a substantially constant value, regardless of the brand of coal, and $\gamma_{100}$ does not have a tendency of convergence and greatly varies according to the brand of coal. Since a linear relationship is observed between surface tension and TI, and $\gamma_{100}$ greatly varies according to the brand of coal, the TI and $\gamma_{100}$ are considered as dominant factors that have an effect on the surface tension of coal.

We studied the relationship between $\gamma_{100}$ and coal properties and found that $\gamma_{100}$ shows a strong correlation with the mean maximum vitrinite reflectance (hereinafter $R_O$) of coal. With TI and $R_O$ as main dominant factors having an effect on the surface tension of coal, it is determined whether the surface tension of coal can be estimated from the measured values of TI and $R_O$. Table 1 shows the properties of the coals G to M, which are used in the determination. $R_O$ is an example physical property value representing a coal rank. Examples of physical property values representing coal ranks other than $R_O$ include the volatile matter of coal, the carbon content, and the re-solidification temperature in softening and melting. These physical property values all show a good correlation with $R_O$. Thus, the volatile matter of coal, the carbon content, or the re-solidification temperature in softening and melting can thus be used as a dominant factor having an effect on the surface tension, instead of $R_O$. These physical property values can be used as an explanatory variable in multiple regression analysis described below.

TABLE 1

| Brand | logMF log/ddpm | $R_o$ % | TI % | Measured Surface Tension mN/m | Estimated Surface Tension mN/m |
|---|---|---|---|---|---|
| G | 2.97 | 1.20 | 20.36 | 40.5 | 40.3 |
| H | 0.48 | 1.56 | 20.96 | 39.1 | 39.2 |
| I | 2.94 | 0.97 | 33.98 | 41.6 | 41.9 |
| J | 2.78 | 0.98 | 47.39 | 42.6 | 42.7 |
| K | 2.77 | 0.97 | 43.40 | 42.6 | 42.4 |
| L | 1.34 | 1.30 | 36.88 | 41.1 | 41.0 |
| M | 1.67 | 1.23 | 22.10 | 40.2 | 40.3 |

In Table 1, "log MF (log/ddpm)" is a common logarithmic value of the maximum fluidity (MF/ddpm) of coals measured by the Gieseler plastometer method described in JIS M8801. "$R_O$ (%)" is a mean maximum vitrinite reflectance of coals G to M in JIS M 8816. "TI (%)" is a total inert content (vol %) and calculated in accordance with Methods of microscopical measurement for the macerals for coal and coal blend in JIS M 8816 and formula (1) based on the Parr formula described in the explanation of the Methods:

Inert content (vol %)=fusinite (vol %)+micrinite (vol %)+(2/3)×semifusinite (vol %)+mineral matter (vol %)　　(1).

The "measured surface tension (mN/m)" is a surface tension (representative value) obtained by measuring semicokes made by treating coals G to M with heat at 500° C. in accordance with the film flotation method. The "estimated surface tension (mN/m)" is an estimated surface tension calculated by using the measured values of $R_O$ and TI and the regression equation including the surface tension (Y) as an objective variable and $R_O$ and TI as explanatory variables ($X_1$, $X_2$).

The coals in Table 1 are examples of coal commonly used as a coke raw material. Coal used as a coke raw material has an MF of 0 to 60000 ddpm (log MF: 4.8 or less), a $R_O$ of 0.6% to 1.8%, and a TI of 3 to 50 vol %. The method of estimating the surface tension of coal according to this example can be suitably used for coals in such ranges.

The regression equation including the surface tension as an objective variable and $R_O$ and TI as explanatory variables can be represented by formula (2):

$$\text{Surface tension} = a + b_1 \times R_O + b_2 \times TI \quad (2).$$

In formula (2), a, $b_1$, and $b_2$ are parameters of the regression equation.

In this example, the measured surface tensions and the measured values of $R_O$ and TI of different brands of coals G to L are subjected to multiple regression analysis to calculate the parameters of formula (2) and thus to obtain regression equation (3):

$$\text{Estimated surface tension} = 42.805 - 3.123 R_O + 0.0614 TI \quad (3).$$

In Table 1, the "estimated surface tension (mN/m)" is an estimated surface tension calculated by using regression equation (3). Coal M is not used to calculate the parameters of regression equation (3), but the estimated surface tension of coal M calculated by using regression equation (3) is substantially the same as the measured surface tension of coal M.

Figure 2:
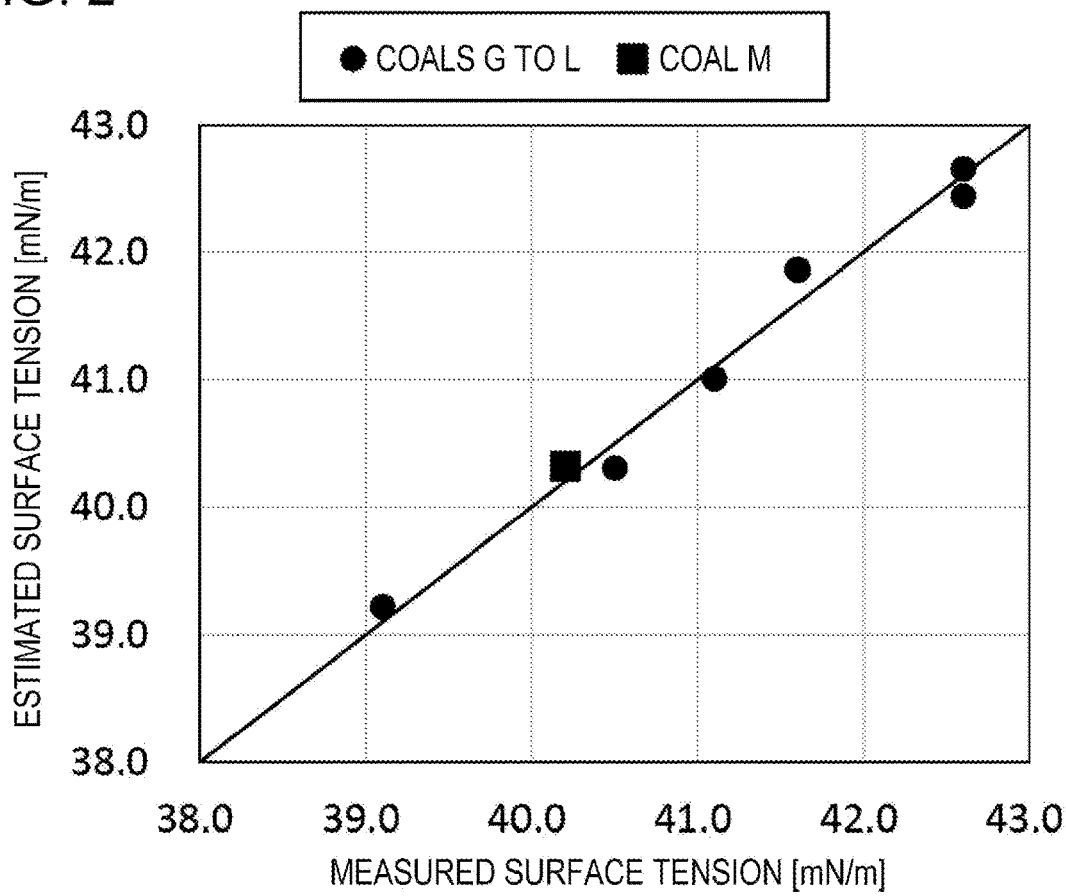
FIG. 2 is a graph showing the relationship between the measured surface tensions and the estimated surface tensions of coals G to M.

FIG. 2 is a graph showing the relationship between the measured surface tensions and the estimated surface tensions of coals G to M. In FIG. 2, the horizontal axis represents the measured surface tension (mN/m), and the vertical axis represents the estimated surface tension (mN/m). In FIG. 2, the solid circle plots represent coals G to L in Table 1, and the solid square plots represent coal M in Table 1. FIG. 2 indicates a very strong correlation between the measured surface tensions and the estimated surface tensions. This result demonstrates that the surface tension of coal can be accurately estimated by using the method of estimating the surface tension of coal according to this example.

FIG. 2 shows an example of estimating the surface tension of coals treated with heat at 500° C., but the heat treatment temperature of coals in this example is not limited to 500° C. To confirm that the method of estimating the surface tension of coal according to this example is not limited to heat treatment at 500° C., it is determined whether the relationship between TI and surface tension shown in FIG. 1 is also established at other heat treatment temperatures. Samples having different TI contents are prepared by the above method using 3 brands (N, O, P) of coal. The samples are converted into semicokes according to the method including (a) to (c) described above under the same conditions except that only the heat treatment temperature is changed to 400° C. and 600° C. The surface tension of each semicoke is measured, and the relationship between TI and surface tension is determined in the same manner as in FIG. 1.

Figure 3:
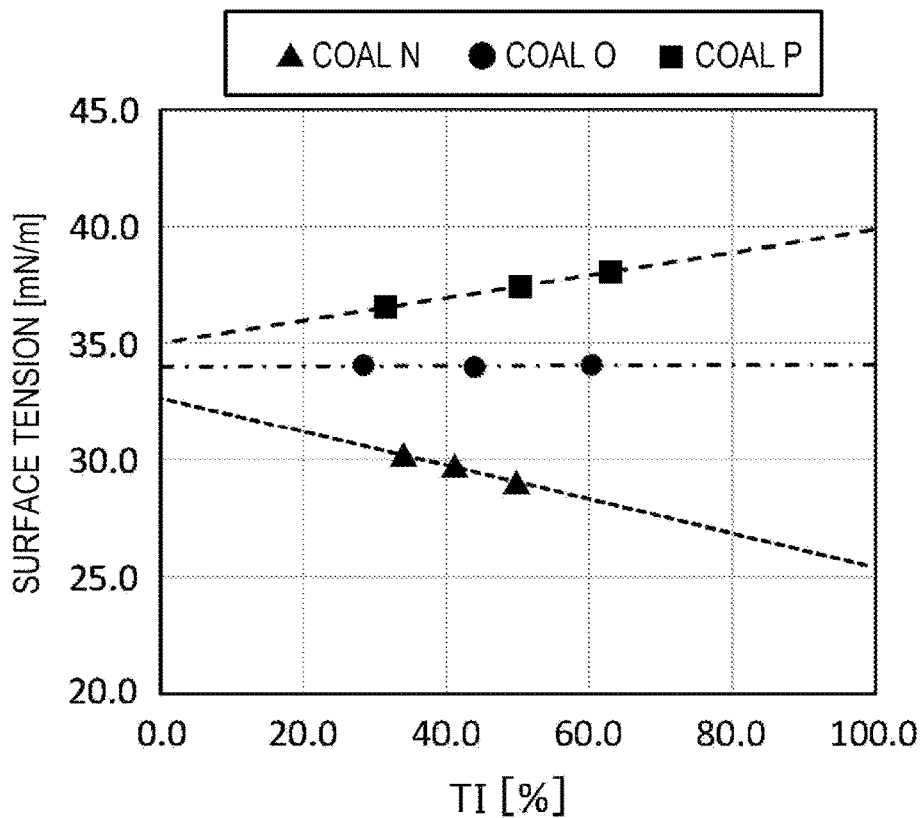
FIG. 3 is a graph showing plots (3 points) of the surface tension of samples having different inert contents and the regression line of the plots for each of 3 brands (N, O, P) of coal with a heat treatment temperature of 400° C.
Figure 4:
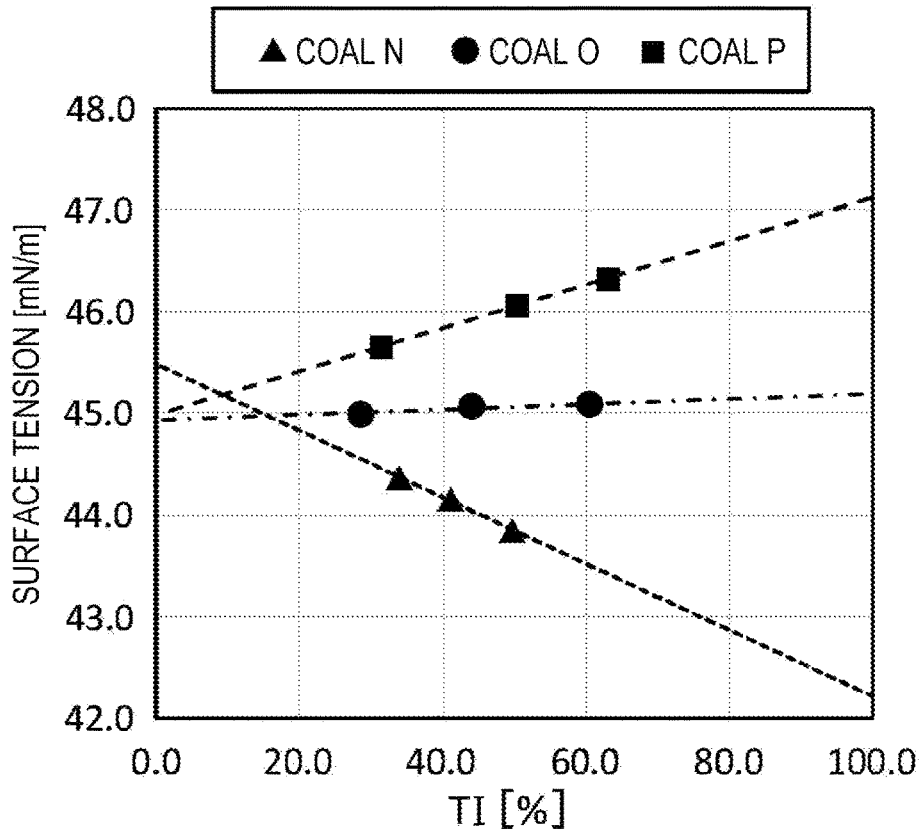
FIG. 4 is a graph showing plots (3 points) of the surface tension of samples having different inert contents and the regression line of the plots for each of 3 brands (N, O, P) of coal with a heat treatment temperature of 600° C.

FIG. 3 is a graph showing plots (3 points) of the surface tension of samples having different inert contents and the regression line of the plots for each of 3 brands (N, O, P) of coal with a heat treatment temperature of 400° C. FIG. 4 is a graph showing plots (3 points) of the surface tension of samples having different inert contents and the regression line of the plots for each of 3 brands (N, O, P) of coal with a heat treatment temperature of 600° C. In FIG. 3 and FIG. 4, the horizontal axis represents TI (%), and the vertical axis represents the surface tension (mN/m).

As shown in FIGS. 3 and 4, a relationship similar to that in FIG. 1 is established between the TI and the surface tension of semicokes prepared at different heat treatment temperatures. This tendency does not change for the same coal. Since a relationship similar to that in FIG. 1 is established between the TI and the surface tension even when the heat treatment temperature is changed, the method of estimating the surface tension of coal according to this example can be used for semicokes prepared at different temperatures.

JP '473 also discloses that the surface tensions of semicokes prepared at heat treatment temperatures of 350° C. or higher and 800° C. or lower show the same tendency regardless of the type of coal. This indicates that our method of estimating the surface tension of coal can be used for semicokes prepared at a temperature of 350° C. or higher and 800° C. or lower as well as semicokes made by a heat treatment at 500° C. In other words, estimation of the surface tension of a coal treated with heat at a predetermined temperature of 350° C. or higher and 800° C. or lower can be done by using the regression equation obtained by multiple regression analysis using the data of surface tensions obtained by treating coals at the predetermined temperature.

In general, coal maceral analysis regarding TI, physical property values representing coal ranks such as $R_o$, and other parameters are widely used in business transactions for the purpose of expressing the characteristics of coal, and these parameters are analyzed and available. Therefore, as long as the surface tension of a coal can be estimated from the coal rank and the TI of the coal, the surface tension of the coal can be estimated without relying on skilled measurers, and the time for measuring the surface tension can be saved.

When regression equation (3) is determined in advance, the measurement of $R_O$ and TI of a coal of which the surface tension is to be estimated allows estimation of the surface tension of the coal. The surface tension of the coal can thus be estimated accurately, easily, and readily by carrying out the method of estimating the surface tension of coal according to this example. The strength of a coke made from a coal blend containing a mixture of coals with different surface tensions is lower than that of a coke made from a coal blend containing a mixture of coals with similar surface tensions. If the surface tension of coal can be estimated in this way, the estimated value of the surface tension can be used to investigate blending of coals. The use of a coal blend having the blending ratio set by the blending investigation to produce coke thus enables production of coke with high quality.

The invention claimed is:

1. A method of estimating a surface tension of coal comprising:
   determining in advance a regression equation including a surface tension of coal as an objective variable and a physical property value and a total inert content as explanatory variables;
   measuring the physical property value and the total inert content of a coal of which the surface tension is to be estimated, and calculating the surface tension of the coal with the measured physical property value and the measured total inert content, and the regression equation; and determining a blending ratio of different brands of coal based on the calculated surface tension to form a coal blend;

wherein the regression equation is represented by formula (2):

$$\text{Surface tension} = a + b_1 \times R_O + b_2 \times TI \quad (2),$$

wherein:

a, $b_1$, and $b_2$ are parameters of the regression equation, $R_O$ is a mean maximum vitrinite reflectance of coal, TI is the total inert content defined in JIS M 8816 and indicates the proportion (vol %) of inerts contained in coal;

wherein the resulting strength of the coke made from the coal blend containing a mixture of coals with different surface tensions is lower than that of a coke made from a coal blend containing a mixture of coals with similar surface tensions.

2. The method according to claim 1, wherein the surface tension is a surface tension of a semicoke made by heating coal to be estimated to a temperature of 350° C. or higher and 800° C. or lower.

3. A method of producing coke comprising:

blending coals having surface tensions estimated by determining in advance a regression equation including a surface tension of coal as an objective variable and a physical property value and a total inert content as explanatory variables;

measuring the physical property value and the total inert content of a coal of which the surface tension is to be estimated, and calculating the surface tension of the coal with the measured physical property value and the measured total inert content, and the regression equation; and determining a blending ratio of different brands of coal based on the calculated surface tension to form a coal blend;

wherein the regression equation is represented by formula (2):

$$\text{Surface tension} = a + b_1 \times R_O + b_2 \times TI \quad (2),$$

wherein:

a, $b_1$, and $b_2$ are parameters of the regression equation, $R_O$ is a mean maximum vitrinite reflectance of coal, TI is the total inert content defined in JIS M 8816 and indicates the proportion (vol %) of inerts contained in coal, to form a coal blend; and carbonizing the coal blend to produce coke;

wherein the resulting strength of the coke made from the coal blend containing a mixture of coals with different surface tensions is lower than that of a coke made from a coal blend containing a mixture of coals with similar surface tensions.

4. A method for producing coke according to claim 3, wherein the surface tension is a surface tension of a semicoke made by heating coal to be estimated to a temperature of 350° C. or higher and 800° C. or lower.

* * * * *